(12) United States Patent
Fröberg

(10) Patent No.: US 6,654,641 B1
(45) Date of Patent: Nov. 25, 2003

(54) HEART STIMULATOR HOUSING HAVING A TUBULAR CONNECTOR

(75) Inventor: Paul Fröberg, Bromma (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/830,241
(22) PCT Filed: Oct. 21, 1999
(86) PCT No.: PCT/SE99/01892

§ 371 (c)(1),
(2), (4) Date: Apr. 24, 2001

(87) PCT Pub. No.: WO00/24461

PCT Pub. Date: May 4, 2000

(30) Foreign Application Priority Data

Oct. 27, 1998 (SE) .............................. 9803692

(51) Int. Cl.[7] .............................. A61N 1/375
(52) U.S. Cl. .......................... 607/37; 439/909
(58) Field of Search .................. 607/37, 38, 36; 439/909

(56) References Cited

U.S. PATENT DOCUMENTS 4,262,982 A   4/1981  Kenny
4,278,093 A   7/1981  Lafortune et al.
4,583,543 A   4/1986  Peers-Travarton
4,934,366 A   6/1990  Truex et al.
5,007,864 A   4/1991  Stutz, Jr.
5,046,242 A   9/1991  Kuzma
5,324,311 A   6/1994  Acken
5,755,743 A * 5/1998  Volz et al. .................. 607/37

FOREIGN PATENT DOCUMENTS

EP   0 242 884   10/1987
GB   1 571 516    7/1980

* cited by examiner

Primary Examiner—Kennedy Schaetzle
(74) Attorney, Agent, or Firm—Schiff Hardin & Waite

(57) ABSTRACT

A metallic pulse generator housing has a tubular connector which receives a proximal lead end plug, the connector being located inside the housing and having a closed end within the housing and an open end welded or bonded to an opening in a wall of the housing. The connector is formed by a metallic barrel which is weldable or bondable to the metallic housing, the barrel being a structurally unitary tube member with a cavity containing electrical contacts for contacting contact surfaces on the lead end plug. At least one insulating substrate, on which the contacts are carried, is arranged in or on a region of a barrel wall which defines the cavity.

15 Claims, 4 Drawing Sheets

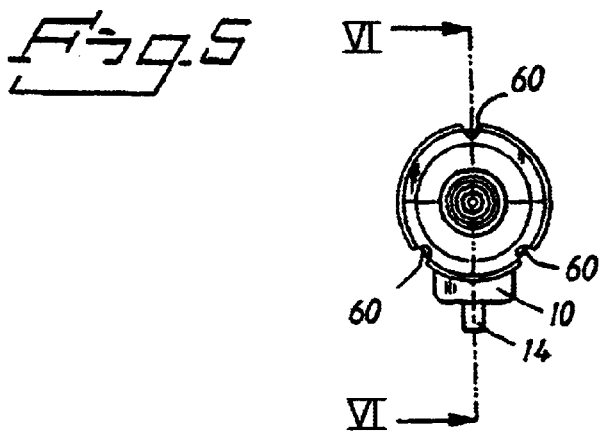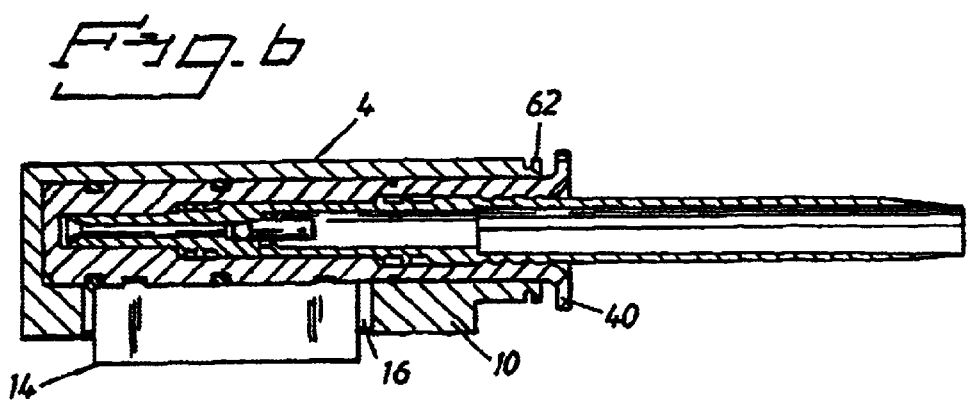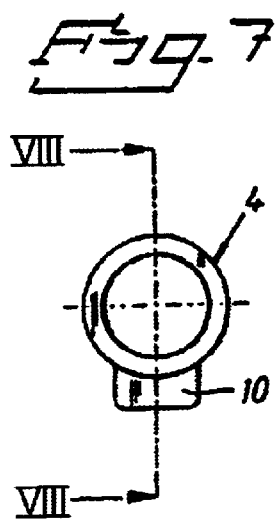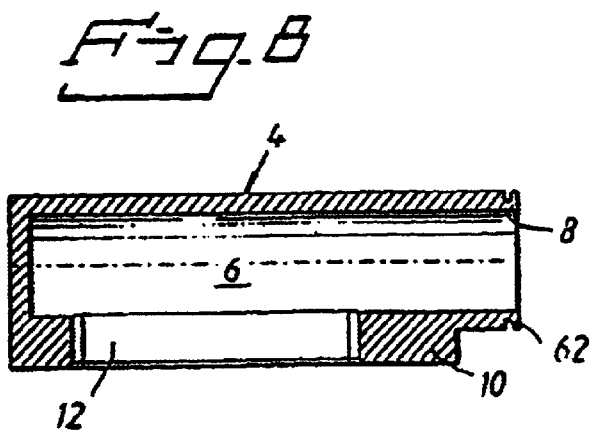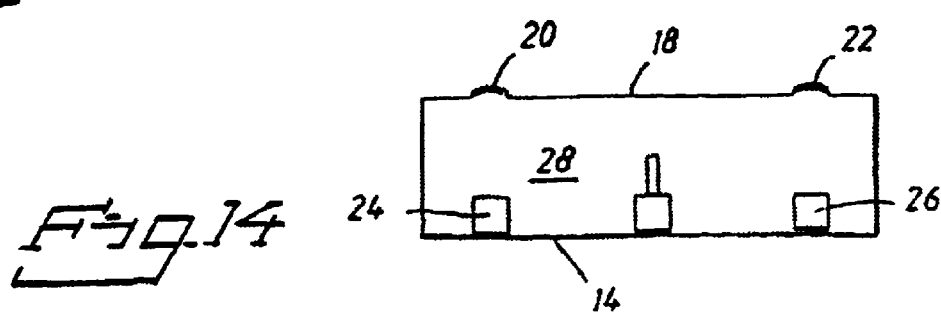

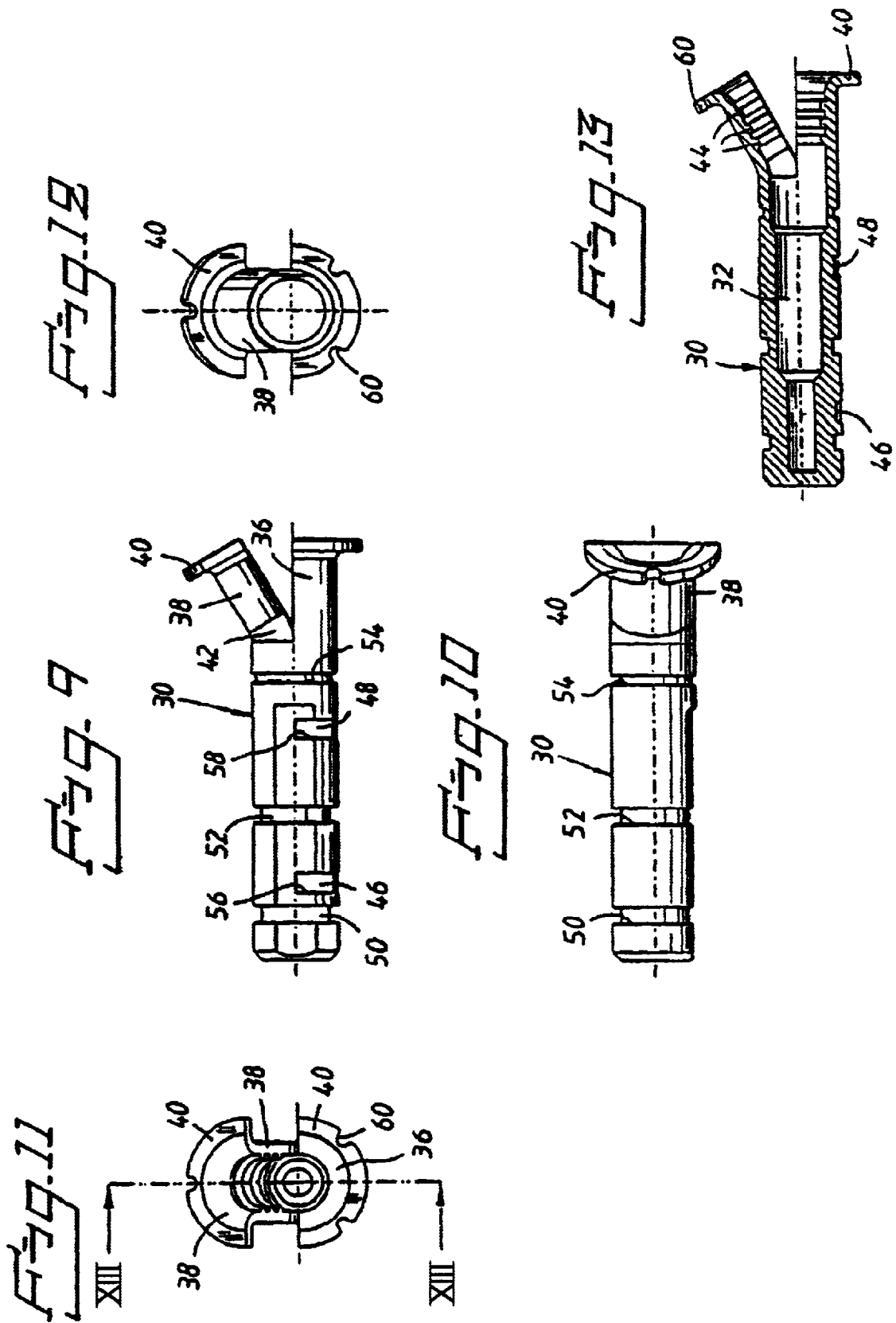

HEART STIMULATOR HOUSING HAVING A TUBULAR CONNECTOR

BACKGROUND OF THE INVENTION

1. Field of the Invention

The present invention is directed to a housing and an electrode lead adapter for a heart stimulator.

2. Description of the Prior Art

An implantable pacemaker (pacer) is a system composed of a pulse generator and the pacing lead(s) connected thereto. At the proximal end of each pacing lead is a male plug (terminal pin) which is connected to the pulse generator, and at the distal end of the lead there is (at least) one electrode adapted to be implanted in (or in the vicinity of) a patient's heart. The pulse generator normally has a housing ("case" or "can"), which contains a battery and electronic circuitry, and a connector ("header"). The connector is a receptacle into which said pacing lead(s) is (are) inserted.

The internal parts of the pacer must be well protected, especially against body fluids, for a long time period. This places strict requirements on all entries into the interior of the housing, especially on the lead connection to the housing. It should also be possible to disconnect the pulse generator from the implanted lead(s), e.g. for replacement or servicing of the generator. The connective parts of the pulse generator and the lead(s) have largely been standardized to include in practice a relatively deep female socket having internal contact surfaces, while the male plug (at the proximal end of each lead) has corresponding external contact surfaces.

Conventionally the connective pulse generator housing part containing the female socket is made of a transparent material, usually a medical grade epoxy resin, which is molded onto the housing and onto contacts protruding from the housing. The lead's male plug is normally locked in the connector receptacle by means of a set-screw or some other fastening means. However, the positioning and alignment of the contact surfaces and of the fastening means or metallic threads for the set-screw, prior to the molding of the connective part, is very complicated, and the delay in the manufacturing process incurred by the curing of the epoxy is considerable.

Thus, it would be desirable that such a molding procedure could be dispensed with.

It has been considered that a possibility of avoiding these problems might be to design a pulse generator which is provided with a female socket located inside its metal housing, however, such an integrated socket, sometimes called a "black hole", is presently not used.

U.S. Pat. Nos. 4,262,982, 4,934,366 and 5,324,311 describe interior sockets or blind holes in pacemaker housings. In all cases the interior socket has a tubular member formed of a number of joined sections of different materials, e.g. metal and insulating ceramics. A metallic end section of the tubular member can be welded or bonded to an opening in the pacemaker housing by means of an exterior flange on the end section. However, the use of sections of different materials in the tubular member makes the assembly procedure more complicated and demanding regarding precision and durability of the components. The integrity of the interior of the housing also must be guaranteed during a very long period of implantation.

U.S. Pat. No. 5,007,864 discloses a lead-to-pacemaker adapter which allows the use of a smaller diameter terminal electrode lead assembly than that for which the pacemaker was designed. The adapter permits direct electrical connection from the terminal pin electrode (at the proximal lead end portion) to the pacemaker connector block and its terminal set screw, without any intermediate connecting elements.

The adapter is tubular and includes a cylindrical body which tapers at its rear open end to an extension. At its forward closed end the adapter has an end face from which an electrically conductive half-round tube extends outwardly. On its underside the adapter has a retaining bump provided for latching the adapter in place within a receptacle cavity in the pacemaker's head portion. Near the outer opening of the receptacle cavity there is a small hole along the bottom side thereof. When the adapter is inserted in place within the receptacle cavity said retaining bump engages within said small hole.

When the terminal pin electrode at the proximal lead end portion has been inserted into the adapter, the pin electrode will be positioned in the channel-shaped half-round tube at the forward end of the adapter. A socket recess set screw, which is threaded into the connector block, is brought into contact and locking engagement with said pin electrode, thereby retaining the lead assembly in firm mechanical and electrical coupling to the pacemaker.

U.S. Pat. No. 4.583.543 discloses an upsizing adapter for electrically and mechanically coupling a small size terminal electrode assembly (which is mounted at the proximal end of a pacing lead) to a large size terminal electrode assembly socket in a pacemaker. The adapter is adapted to be inserted into the electrode assembly socket in the pacemaker, and the electrode assembly at the proximal end of the pacing lead is inserted into a socket in the adapter. Thus, the smaller terminal electrode assembly at the lead's proximal end is received and held in a larger size socket in the pacemaker by means of the adapter. The adapter with the pacing lead electrode assembly inserted therein is retained in the pacemaker socket by means of an Allen set screw in a connector block within an upper body portion of the pacemaker. A pointed tip of the set screw forces a side wall portion of the adapter's forward end tube (enclosing the lead's terminal pin electrode) into contact with the lead's terminal pin electrode. In this way, an electrical and mechanical connection is provided between the pin electrode and the connector block.

SUMMARY OF THE INVENTION

A primary object of the invention is to provide a tubular connector for a pulse generator housing that is suitable for so called black holes.

A further object is provide a connector which produces a mechanically locking, electrical connection of a proximal lead end portion to the lead connection unit in a pacemaker or some other type of pulse generator.

Another object of the invention is to design a tubular connector, as well as an adapter suitable for that type of connector, which facilitates the connection of an undersized proximal lead end electrode assembly to the receiving cavity of the lead connection unit of a heart stimulator.

A still further object is to provide a connector including a tubular, male plug receiving member or barrel being designed to be optimized from a manufacturing as well as a strength-of-material standpoint.

The above objects are achieved in accordance with the principles of the present invention in a metallic pulse generator housing having a tubular connector adapted to receive a proximal lead end plug, the connector being located inside the housing and having a closed end within the housing and an open end that is welded or bonded to an opening in a wall of the housing. The connector is formed by a metallic barrel which is weldable or bondable to the metallic housing, and has a structurally unitary tube member with a cavity containing electrical contacts for contacting contact surfaces on the lead end plug. At least one insulating substrate is arranged in or on a region of the barrel wall which defines the cavity. The substrate has contacts on a surface thereof facing into said cavity.

DESCRIPTION OF THE DRAWINGS

FIG. 5 shows an end view of the inventive connector in fully assembled state.

FIG. 6 shows a longitudinal section through the connector in FIG. 5. at plane VI—VI thereof.

FIG. 7 shows an end view of the barrel of the tubular connector in FIGS. 1–6.

FIG. 8 shows a longitudinal section through the barrel in FIG. 7, at plane VIII—VIII thereof.

FIG. 9 shows a bottom view of the adapter of the tubular connector in FIGS. 1–6.

FIG. 10 shows a side view of the adapter in FIG. 9.

FIG. 11 and FIG. 12 show end views of the right and left ends, respectively, of the adapter in FIG. 9.

FIG. 13 shows a longitudinal section through the adapter in FIG. 11, at plane XIII—XIII thereof.

FIG. 14 shows (on a larger scale) a side view of the substrate slab of the connector in FIG. 4.

DESCRIPTION OF THE PREFERRED EMBODIMENTS

Figure 1:
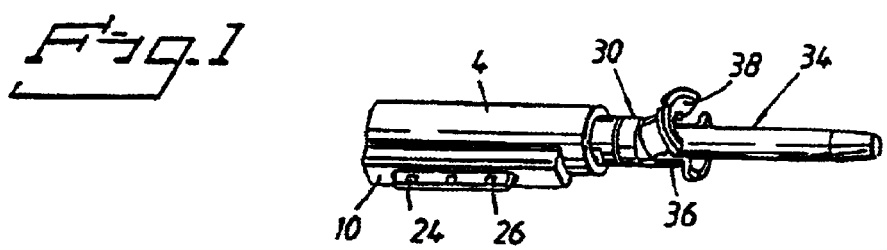
FIG. 1 shows a perspective view of a partly assembled tubular connector according to the invention.

A preferred embodiment of a metallic housing with tubular connector according to the invention will now be described with reference to FIGS. 1–6 and the three major components thereof are depicted separately in FIGS. 7–8, 9–13 and 14, respectively.

In FIGS. 1, 2, 4 and 6 a tubular connector 2 is shown in a partly assembled state. The connector, which is adapted to form part of a lead connection unit 100 of a heart stimulator or pulse generator schematically shown in FIG. 15, has a metallic barrel 4 with a cavity 6 having an entrance opening 8 at its rear end (right end in FIGS. 4 and 8). In a thickened side wall portion 10 of the barrel 4 there is formed an elongated, longitudinal through opening 12 between the cavity 6 and the outside of the barrel. A rectangular slab or substrate 14 of ceramic material is sealingly fastened in opening 12, e.g. by brazing solder 16. On its narrow longitudinal top side 18 the slab 14 is provided with two spaced apart contacts 20, 22 with convex surfaces that are metallized with e.g. gold. These contacts are individually electrically connected to a pair of external pads 24, 26 on a lateral surface 28 of the slab, see FIGS. 1 and 14.

The substrate 14 may, however, alternatively be an integral part of the substrate carrying the internal electronics of the pacer, this substrate thus extending into the opening 12 and being sealingly fastened thereto. In the case of a pacer with two connectors, the connectors could be located on opposite sides of the electronics substrate with the substrate extending into the respective openings 12. In both cases, separate conducting means connecting the internal electronics with the barrel would not be necessary. This design of course could be used regardless of whether the embodiment utilizing the adaptor part is used or an embodiment is used in which the means connecting the substrate with the male connector are permanently mounted in the barrel.

Figure 2:
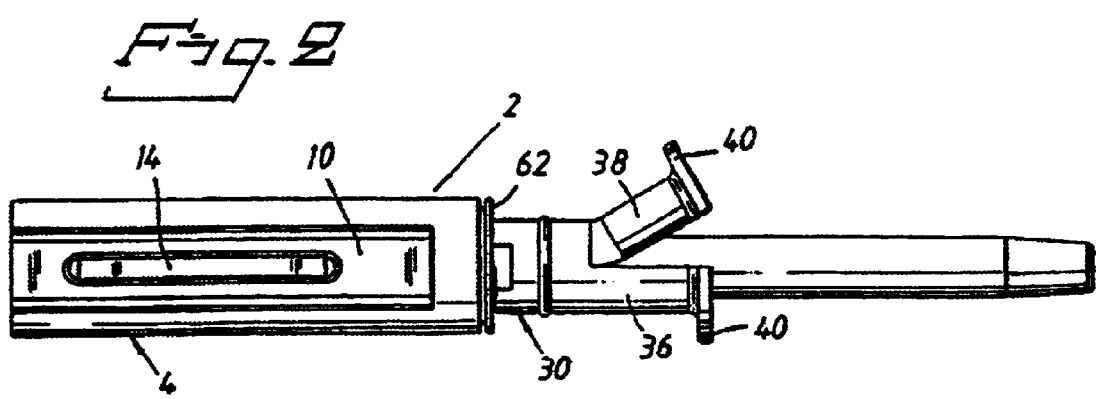
FIG. 2 shows (on a larger scale) a bottom view of the connector in FIG. 1.
Figure 3:
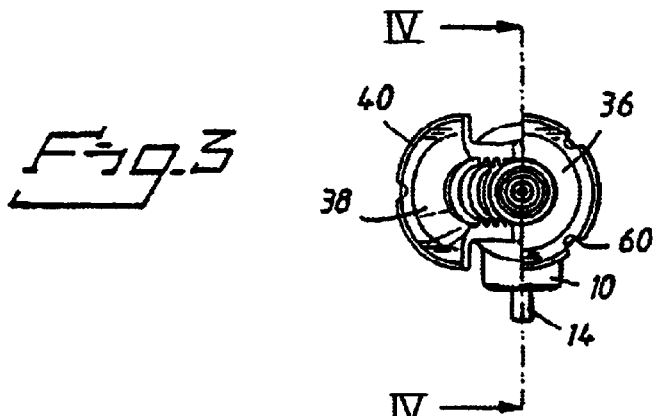
FIG. 3 shows an end view of the connector in FIG. 2.
Figure 4:
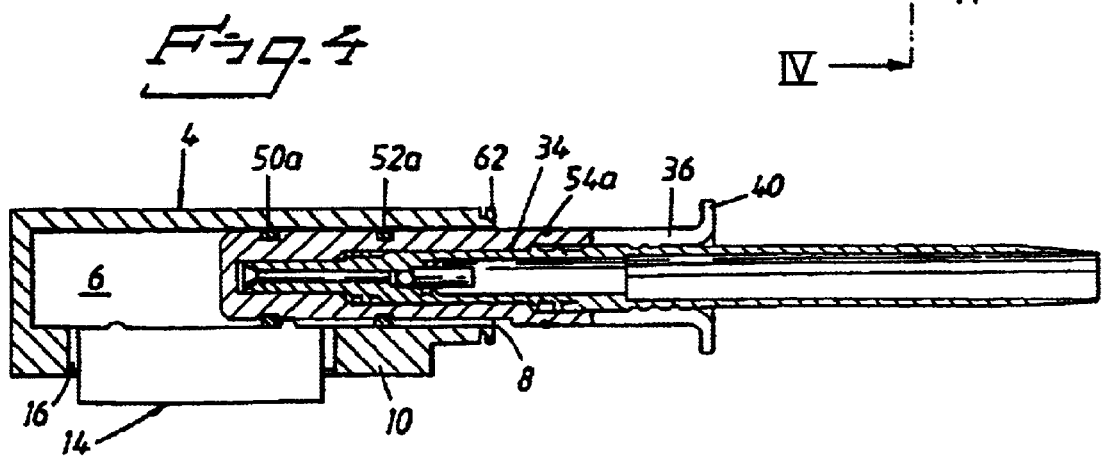
FIG. 4 shows a longitudinal section through the connector, at plane IV—IV in FIG. 3.

As shown in FIGS. 1, 2 and 4 a tubular adapter 30 is insertable and sealingly lockable in the barrel cavity 6. This adapter, which constitutes a casing with a central bore 32, is made of an elastic, electrically insulating material, e.g. a semi-soft elastomer, which may be transparent to allow easy visual supervision of the position of a proximal lead end portion 34 which is inserted into the adapter bore 32. The rear end portion of the adapter is axially split open into two half-shells 36, 38. Each half-shell has an outward flange 40 at its rear end. As visible in FIGS. 1–3 and 9–13 one half-shell 38 is elastically and flexibly connected with the rest of the adapter by a transition portion 42.

The half-shells 36, 38 are provided, on the insides thereof, with a locking mechanism adapted to lock the proximal lead end portion 34 in its fully inserted position in adapter bore 32 when also the adapter itself has been fully inserted into the barrel cavity 6. This locking mechanism includes circumferential engagement elements, e.g. ribs 44, which are brought into engagement with the lead end portion 34 when the half-shell 38 is turned down (from its angular position shown in FIGS. 1–3) to its axial engagement position obtained by fully inserting the adapter 30 into barrel cavity 6, as shown in FIG. 6.

Furthermore, to space apart and mutually seal the electrical pole surfaces 46, 48 on the outside of the adapter tube or casing from each other in barrel cavity 6, the adapter is provided, on the outside thereof, with axially spaced apart circumferential grooves 50, 52, 54 (see FIGS. 9, 10, 13) adapted to accommodate 0-ring type sealing elements 50a, 52a, 54a (see FIGS. 4 and 6).

When the adapter 30, with the lead end portion 34 fully inserted therein (as in FIG. 4), has been axially fully inserted in barrel cavity 6 (as in FIG. 6), the adapter is positively locked in position therein by being turned clockwise 90°, so that slots 56, 58 (which contain the pole surfaces 46, 48) will slide onto the convex contacts 20, 22 on slab 14. Thereby the adapter will become mechanically locked in position in cavity 6, and the metal parts (e.g. thin metal leafs carrying pole surfaces 46, 48) molded in the elastomeric adapter will become electrically connected to the convex or spherical, metallic contacts 20, 22 on the ceramic material slab 14.

To facilitate the 90° turning of the adapter, the flanges 40 of the two half-shells 36, 38 are provided, at the edges thereof, with a suitable number of notches 60 adapted to be engageable by means of an external, simple, adapter turning tool (not shown on the drawings). To turn the adapter this tool is merely folded around the lead end portion 34 and fit into the notches 60 in the adapter flanges 40, whereupon the adapter can be turned 90° to its definite locking position.

The tubular connector 2 is adapted to form part of a lead connection unit of a heart stimulator or pacemaker. Such a unit can be positioned in a header or specific receptacle part of a pacemaker, or in a "black hole" cavity provided in the actual pacemaker housing or can. To facilitate the installation of the tubular connector according to the invention in a header or such black hole, the barrel 4 preferably is provided with a circumferential flange 62 in the region of its entrance opening 8. By means of this flange the adapter can be attached easily to the pacemaker can, e.g. by laser welding.

Figure 15:
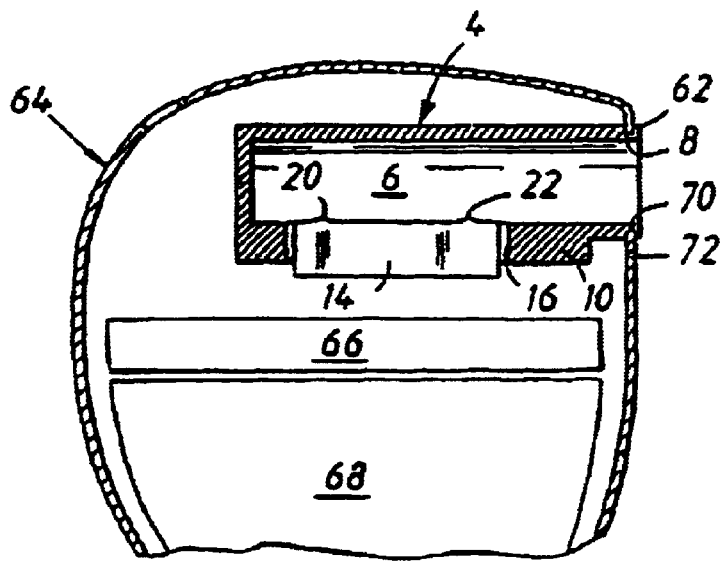
FIG. 15 shows a cutaway side view of a pulse generator with a tubular connector barrel mounted in the upper part of the pulse generator housing.

In FIG. 15 there is shown a pacemaker housing or can 64 containing a connector barrel 4, electrical circuits 66 and a battery 68. In this case the barrel 4 is mounted in an opening 70 in a side wall portion 72 of the upper part of the housing 64. The barrel 4 is attached to the wall portion 72 by means of the circumferential flange 62 which is laser welded to the wall portion. The preferably cylindrical cavity 6 within the barrel 4 is adapted to receive and support an adapter 30 (having a proximal lead end portion inserted therein), in the way shown in FIG. 6. Thus, the socket configuration shown in FIG. 15 is of the "black hole" type. A substrate 14, which is made of an electrically insulating material and provided with contacts 20. 22, is sealingly fastened in a longitudinal through opening in a thickened wall portion 10 of the barrel 4.

Figure 16:
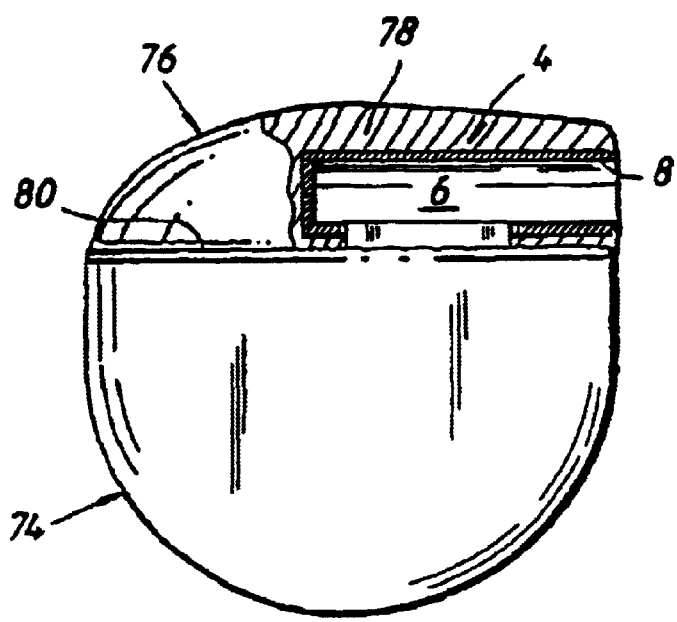
FIG. 16 shows a partially cutaway side view of a pulse generator with a tubular connector barrel included in a specific receptacle part (header) of the generator.

In FIG. 16 there is shown a more conventional pacemaker having a housing or case 74 with a specific receptacle part or header 76 attached thereto. This header 76 may e.g. be an epoxy resin body 78 molded on a planar top surface 80 of case 74. The tubular connector barrel 4 may be embedded in epoxy body 78 from the very molding thereof or may be inserted afterwards in a cylindrical cavity formed in the molded body.

In the preferred embodiment described above, the cavity having the insulating substrate has been illustrated as being located laterally in the envelope surface of the tubular connector (which in the preferred embodiment is cylindrical). It should be noted that the insulating substrate of course could be located in the end of the connector for instance forming a plug brazed or soldered into the end of the connector. The inner side of the plug then could carry the spaced-apart contact surfaces, which for instance could be arranged concentrically on said inner surface and which would be in electrical connection with the exterior of the tubular connector. The tubular adapter would be provided with corresponding exterior contacts on the outer end surface being in electrical connection with the contacts on the inside of the adapter. In other respects the design would be similar to the design described in the preferred embodiments with lateral slots and lugs forming a bayonet joint between the adapter and the connector.

Although modifications and changes may be suggested by those skilled in the art, it is the intention of the inventor to embody within the patent warranted hereon all changes and modifications as reasonably and properly come within the scope of his contribution to the art.

What is claimed is:

1. In a metallic pulse generator housing having a tubular connector adapted to receive a proximal end plug of an electrode lead, said connector being disposed inside said housing and having a closed end within said housing and an open end attached to an opening in a wall of said housing, the improvement of said connector comprising:

a metallic barrel attached to said metalic housing and formed by a structurally unitary tube member having a cavity containing electrical contacts adapted for respectively contacting contact surfaces on said proximal end plug, said metallic barrel having a barrel wall defining said cavity; and an insulating substrate, carrying said electrical contacts, disposed at a portion of said barrel wall.

2. The improvement of claim 1 wherein said substrate is disposed in said barrel wall.

3. The improvement of claim 1 wherein said substrate is disposed on said barrel wall.

4. The improvement of claim 1 wherein said cavity has an entrance opening at said open end of said connector and wherein said barrel wall comprises a side with a through opening therein providing communication between said cavity and an exterior of aid barrel, and wherein said improvement further comprises:

a tubular adapter insertable into and sealingly lockable in said cavity, said adapter being composed of electrically insulating material and having a rear end portion having a locking mechanism adapted to lock said proximal end plug within said adapter when said proximal end plug is inserted into said adapter and when said adapter is fully inserted in said barrel cavity; and wherein said substrate is sealingly fastened in said opening in said side wall of said barrel and wherein said contacts carried by said substrate mate with contact elements at an exterior of said adapter when said adapter is fully inserted in said cavity.

5. The improvement of claim 4 wherein said through opening is an elongated, longitudinal opening in a thickened side wall of said barrel, and wherein said substrate is a unitary substrate element at least partially disposed in said longitudinal opening and positively fixed in said opening.

6. The improvement of claim 5 wherein said substrate is a slab of ceramic material having a narrow longitudinal al side with two spaced-apart contacts respectively having convex surfaces adapted to contact with said mating contact elements at said surface of said adapter, said contacts on said slab being individually electrically connected with ads disposed at a surface of said slab at said exterior of said barrel.

7. The improvement of claim 4 wherein said through opening comprises at least two spaced-apart openings a thickened side wall of said barrel, and wherein said substrate comprises respective substrate elements in each of said spaced-apart openings, each substrate element being at least partially disposed in the respective opening and positively fixed therein.

8. The improvement of claim 4 wherein said adapter has a casing with a central bore with an entrance opening adapted for insertion of said proximal end plug, and wherein said rear end portion of said adapter is axially split into two half-shells, at least one of said half-shells being elastically connected with a remainder of said adapter and having an outward flange at said rear end.

9. The improvement of claim 8 wherein each of said half-shells has a shell rear end, and wherein each of said half-shells has an outward flange at its shell rear end, each flange having an edge with at least one notch therein adapted for engagement with an externally applicable adapter turning tool.

10. The improvement of claim 8 wherein said adapter, on an inside of each of said half-shells, has circumferential engagement elements adapted for engagement with said proximal end plug when said two half-shells are closed and locked around said proximal end plug.

11. The improvement of claim 8 wherein at least one of said half-shells subtends an acute angle with a longitudinal axis of said adapter when said rear end portion of said adapter is free and not inserted into said cavity of said barrel.

12. The improvement of claim 4 wherein said adapter is comprised of elastic material.

13. The improvement of claim 12 wherein said adapter is comprised of a semi-soft elastomer.

14. The improvement of claim 12 wherein said adapter is comprised of transparent elastic material.

15. The improvement of claim 4 wherein said adapter has an exterior having axially spaced circumferential grooves with respective sealing elements therein.

* * * * *